United States Patent [19]

Zurcher

[11] 4,280,506

[45] Jul. 28, 1981

[54] DIGITAL WATCH/INFRARED PLETHYSMOGRAPH HAVING A REMOVABLE PULSE SENSOR UNIT FOR USE WITH A FINGER CUFF EXTENSION

[75] Inventor: Rudolf F. Zurcher, Newport Beach, Calif.

[73] Assignee: Hughes Aircraft Company, Culver City, Calif.

[21] Appl. No.: 39,532

[22] Filed: May 16, 1979

[51] Int. Cl.$^3$ ............................................. A61B 5/02
[52] U.S. Cl. .................................................. 128/690
[58] Field of Search ........................ 128/633, 687–690

[56] References Cited

U.S. PATENT DOCUMENTS

| | | | |
|---|---|---|---|
| 3,646,931 | 3/1972 | Phelps et al. | 128/689 |
| 3,742,938 | 7/1973 | Stern | 128/687 |
| 4,129,124 | 12/1978 | Thalmann | 128/690 |
| 4,163,447 | 8/1979 | Orr | 128/690 |
| 4,185,621 | 1/1980 | Morrow | 128/690 |

OTHER PUBLICATIONS

Anon., "IR Sensor Built into Watch Measures the Wearer's PR," *Electronics*, vol. 5, No. 9, Apr. 28, 1977, pp. 32, 34.

Anon., "LCD Watch Doubles as a Heart Monitor," *Electronics*, Mar. 1, 1979, pp. 42–43.

*Primary Examiner*—Robert W. Michell
*Assistant Examiner*—Francis J. Jaworski
*Attorney, Agent, or Firm*—Lewis B. Sternfels; W. H. MacAllister

[57] ABSTRACT

A digital watch having a face mounted detachable pulse sensor unit coupled to infrared plethysmograph electronics within the watch. The pulse sensor unit is detachable from a receptacle on the watch face and mountable into a receptacle at a first end of a remote pulse sensing cable. The second end of the cable is connected into the watch receptacle for conveying the pulse sensing information to the infrared electronics. A cuff holds the pulse sensor unit in place against the wearer's finger for sampling his heartbeat. The wearer may thus monitor his pulse rate while both hands are free.

17 Claims, 8 Drawing Figures

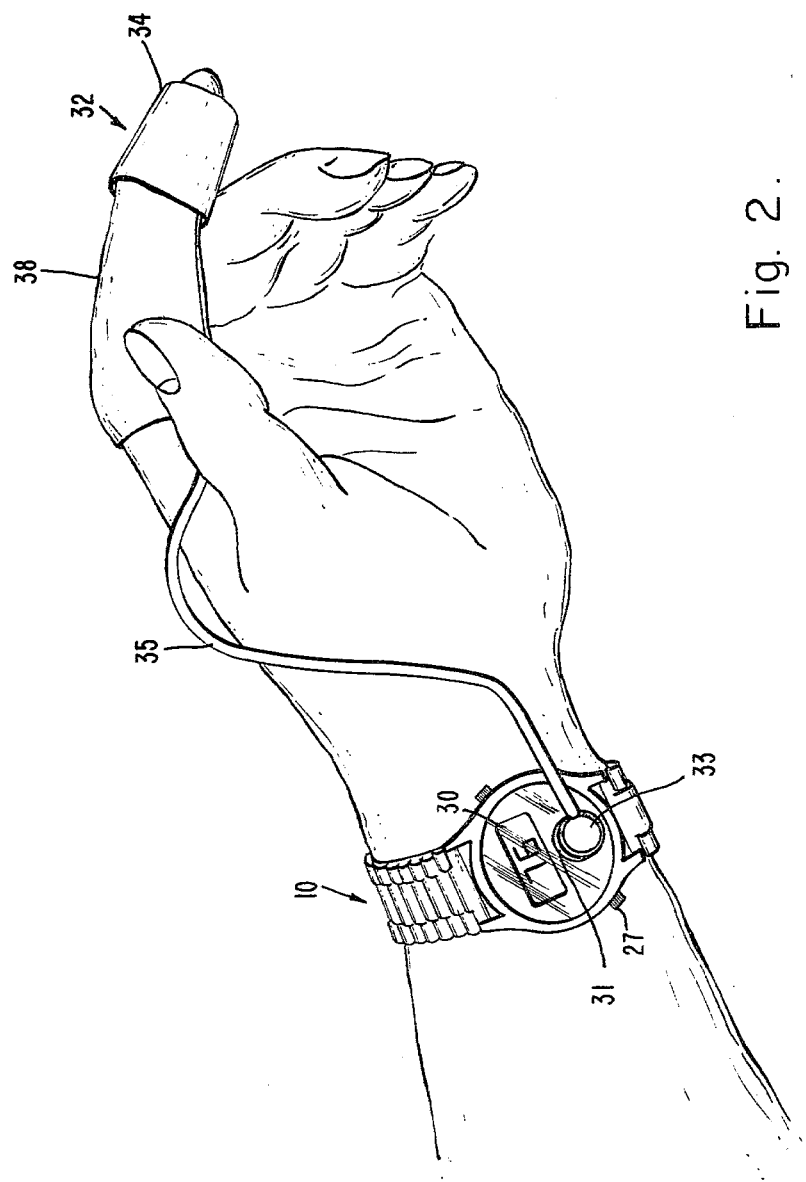

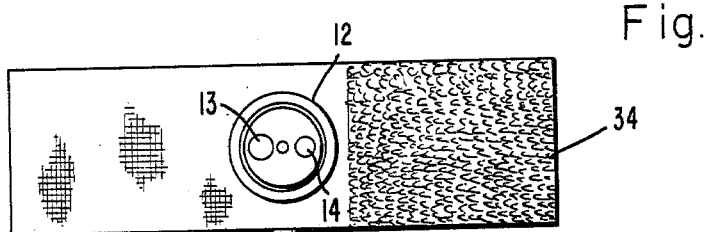
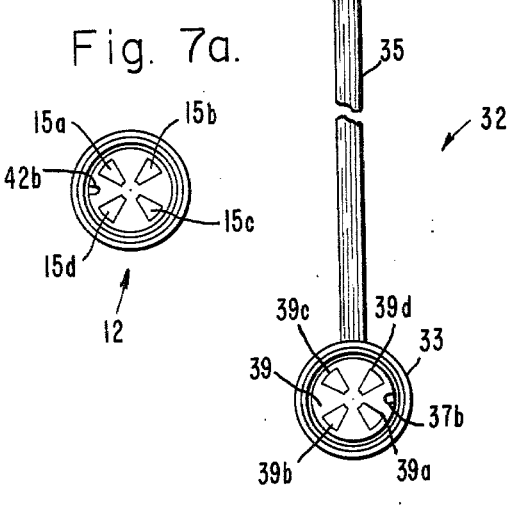
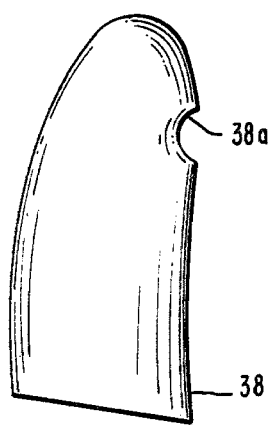
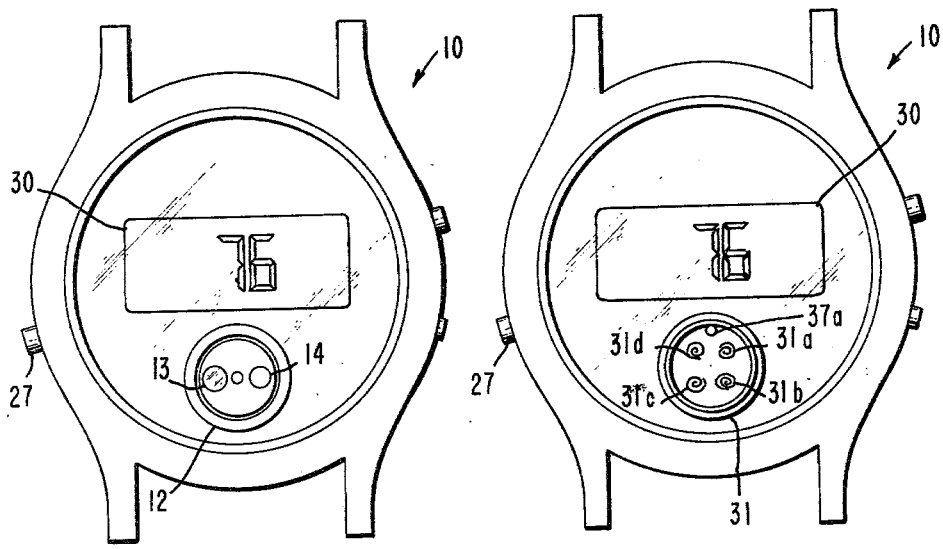

DIGITAL WATCH/INFRARED PLETHYSMOGRAPH HAVING A REMOVABLE PULSE SENSOR UNIT FOR USE WITH A FINGER CUFF EXTENSION

BACKGROUND OF THE INVENTION

1. Field of the Invention

The invention relates generally to a digital watch having an infrared plethysmograph and in particular it relates to a remote pulse sensor cable for use with a pulse sensing digital watch.

2. Description of the Prior Art

Pulse sensing digital watches are relatively new to the field, but nonetheless, their principles of operation are well known and understood. One of the first pulse sensing watches on the market utilizes an infrared pulse sensor, mounted on a watch face, connected to special electronics within the watch. The wearer activates the plethysmograph electronics merely by pushing a button switch on the edge of the watch case, then places his fingertip over the infrared sensor and reads his pulse rate directly from the digital display.

Pulse rate sensing is dependent upon certain physiological changes which occur during each cardiac cycle, i.e., the diastole and the systole. In the diastole phase the cavities of the heart expand and fill with blood. The diastolic pressure is the lowest arterial blood pressure of a cardiac cycle occurring during the diastole of the heart. In the systole phase, the heart contracts, forcing the blood onward, thus keeping the circulation up. The systolic pressure is the highest arterial pressure of a cardiac cycle. The fresh blood supply from the heart is conducted by arteries, thence by capillaries. Veins return the blood supply to the heart. Blood in the arteries and capillaries is under pressure and flows in waves due to the beats of the heart. In response to the systole of the heart, the pressure in the arterial/capillary system increases to its maximum value and the system fills with the blood being pumped out of the heart. During diastole, the heart fills with blood from the veins as the pressure drops in the arterial/capillary system and the amount of blood in this system decreases.

One's finger tips contain a great number of these tiny capillaries which fill with a fresh blood supply during the systolic phase and empty during the diastolic phase. Heart-rate measurement relies on the slight increase in infrared light absorption by the blood in the capillaries of the finger-tip during the systolic pressure wave.

An infrared plethysmograph within a digital watch may include a light emitting photodiode which emits either a continuous or a pulsed infrared signal which is directed at the capillaries in the fingertip. The IR reflected from the capillaries is detected by an infrared detector such as a photodiode or phototransistor. The IR detector is coupled to a microcomputer within the watch case. As explained above, the capillaries are more reflective of IR energy during the diastole than the systole. The microcomputer measures the differences in the signals reflected by the capillaries, counts the intervals between them, amplifies the data, averages the calculated heartbeat and displays it periodically after a predetermined number of heartbeat counts.

The reasons for wearing such a pulse sensing watch may be as varied as the number of individuals wearing them. But generally, most persons are interested in knowing their pulse while at rest, to indicate their degree of relaxation, or during some activity, to determine, at least indirectly, the stress they place on their hearts. Sampling one's own pulse rate at rest is a simple procedure. The wearer merely turns the sensing electronics on, places his finger over the infrared sensor gently, and reads his pulse directly from the display. It is necessary to apply a constant and light finger pressure against the infrared sensor, otherwise false readings may occur. If too much pressure is applied, circulation through those capillaries may be severly curtailed and low pulse readings would result. If insufficient finger pressure is applied, the wearer's finger may move relative to the sensor thereby giving false readings.

In order for one to have a more accurate reading of one's pulse during an activity the pulse should be read during that activity. Although a high heart-beat rate during a strenuous activity is not immediately reduced upon cessation of that activity, the heart does tend to slow down rapidly when the activity is terminated. Therefore, it is most desirable to sample one's pulse during the most strenuous phases for an accurate determination of the stress one places on one's heart.

Monitoring one's pulse in the course of some activities may be difficult because of the pressure requirements explained above. For example, a runner while running places a finger of his right hand on the wristwatch sensor worn on the left arm and hopes that he is applying the proper pressure. This is a rather clumsy and awkward attitude. More than likely the readings obtained would be inaccurate due to the pressure requirements. In order to obtain precise readings, that person would have to stop and take his pulse. However, when he stops, his heart has started its slowing process and the readings he obtains are not representative of his previously higher heart beat.

OBJECTS AND SUMMARY OF THE INVENTION

Accordingly, it is an object of the present invention to provide a simple, reliable heartbeat monitoring system.

It is another object of the present invention to provide a pulse monitor having remote sensing.

It is yet another object of the present invention to provide a pulse sensor and display operable with one hand.

It is still another object of the present invention to provide a pulse sensor and display for monitoring heartbeat during activities requiring both hands to be free.

It is yet another object of the present invention to provide a remote pulse sensing device for applying a constant pressure for accurate pulse sensing.

It is still another object of the present invention to provide a device for shielding a remote pulse sensor from ambient infrared signals.

In accordance with the foregoing objects, infrared pulse sensing electronics, suitable for wearing, has a receptacle for alternately receiving either a detachable pulse sensor unit or a connector connected to one end of a remote pulse sensing cable. The detachable pulse sensor unit is mountable to a receptacle at the second end of the remote pulse sensing cable. The pulse sensor unit, when attached to the second end of the cable, is held in place against the wearer's skin by a cuff for remotely sensing the wearer's pulse rate.

BRIEF DESCRIPTION OF THE DRAWINGS

FIG. 2 is a perspective view illustrating a pulse sensing watch and the remote sensor being worn.

FIG. 3 is a side view of a pulse sensor shield.

FIG. 4 is a plan view of the watch illustrating a pulse sensor.

FIG. 5 is a plan view illustrating the watch with the pulse sensor removed from the watch receptacle.

FIG. 6 is a plan view of the remote sensing cable assembly.

FIG. 7a is a plan view of the contact side of a remote pulse sensor.

DETAILED DESCRIPTION OF THE DRAWINGS

Figure 1:
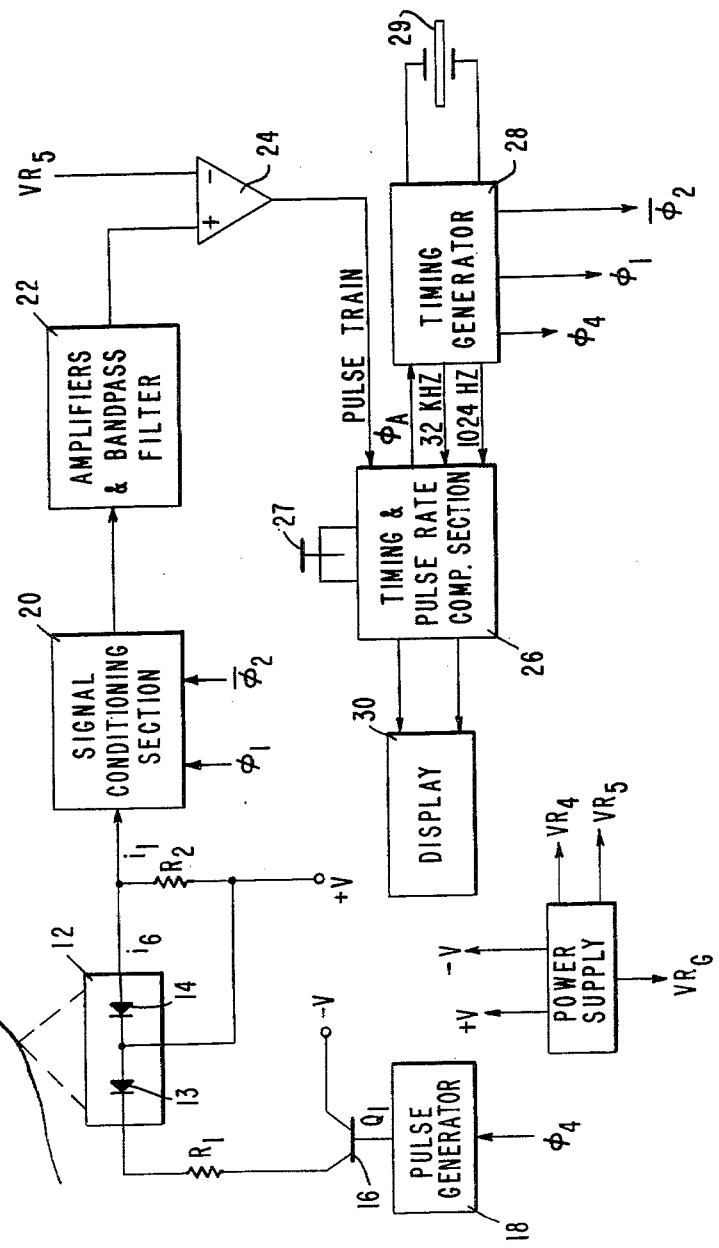
FIG. 1 is a schematic block diagram illustrating a heart pulse sensing system.

FIG. 1 illustrates an infrared plethysmograph system 10 as might be found in a digital watch. The sensor 12 includes a light emitting photodiode 13 which transmits either a continuous wave IR signal or a pulsed IR signal. Another photodiode 14 is situated next to the transmitting diode 13, for receiving the reflected IR energy. The transmitter 13 is powered by a transistor 16 which is controlled by a pulse generator 18. The transmitter 13 emits a pulsed infrared signal which is directed to the finger's capillaries beneath the skin. Depending on the phase of the pressure wave, either diastolic or systolic, the transmitter signal will be more or less reflected to the receiver 14. The signal conditioning section 20, directly coupled to the receiver 14, cancels asynchronous ambient light.

The signal conditioning section 20 is coupled directly to an amplifier and bandpass filter 22. The amplifier/filter 22 amplifies and filters the systolic pressure wave pulses which typically occur 60 to 80 per minute but which could easily double during periods of strenuous exercise and sometimes exceeds 200 pulses per minute. The amplifier/filter 22 in combination with the signal conditioning section 20 provides the pulse counting function for the system.

The output signal of the amplifier/filter 22 is provided to the positive input terminal of a voltage level discriminator 24. The discriminator 24 compares the input signal, at its positive input terminal, with a reference voltage $VR_5$ at its negative input terminal, which sets the detection level for the systolic pulses. A train of pulses representative of the heartbeat rate is transmitted to the digital watch timing and pulse rate computation section 26 which detects the time between the pulse edges such as the positive-going leading edges of the systolic pulses in the train. It then computes the pulse rate. The type of computations provided by the section 26 is well known in the digital art and need not be explained in further detail. The pulse rate is then displayed as a decimal number by the digital watch's displays section 30.

A timing generator 28 responds to a crystal oscillator 29 and provides the timing $\phi_1$, $\bar{\phi}_2$ and $\phi_4$ as well as a 32KHZ clock signal and a 1024HZ signal to the computation section 26. The timing signals $\phi_1$ and $\bar{\phi}_2$ are applied to signal conditioning section 20 for providing carrier cancellation during the sampling pulse periods. The clock pulse signals $\phi_4$ are used to drive the transmitter 13 at a constant rate such as 73HZ.

Depressing the push button switch 27 once causes the timing and pulse rate computation section 26 to generate an analog power control signal $\phi_A$ which in turn causes the timing generator to produce the timing and control signals which control the plethysmograph. Pressing the push button 27 a second time causes the analog signal $\phi_A$ to be turned off, thus turning the pulse monitoring function off.

A more detailed discussion of an infrared plethysmograph may be found in copending applications Ser. Nos. 6,983 and 965,816 for "Measurement System Having Pole Zero Cancellation" and "Heart Rate Measurement System" by Lanny L. Lewyn and assigned to the assignee of the present application.

Referring now more specifically to the invention, FIG. 2 illustrates an infrared plethysmograph digital watch 10 being worn on the inside of an individual's wrist for purposes of discussion. It is not necessary to position the watch thusly for measuring one's pulse. In addition, the remote sensor is shown here applied to the index finger, but it could be applied to any other finger where it would be less of an interference with activities of the hand. To utilize the remote sensor, the detachable pulse sensor unit 12, shown in FIG. 4, is removed from the connector receptacle 31 on the watch face, as illustrated in FIG. 5. Then, see also FIGS. 2 and 6, connector 33 at one end of a remote pulse sensing cable arrangement 32 is secured to the connector receptacle 31 on the watch 10 in place of the pulse sensor unit 12. Finally, the pulse sensor unit 12, which had been removed from the watch, is secured to a sensor receptacle 36 (see FIG. 7) at the other end of the cable arrangement 32 where it is held in place against the wearer's finger by a cuff 34 (see FIGS. 2 and 6). The cable 35 itself may be either a three or four wire cable or flexible circuit which connects the connector 33 with the sensor receptacle 36. An optional finger boot or shield 38 may be slipped over the wearer's finger before the sensor bearing cuff is applied to the finger. The boot 38 has an opening through which the sensor unit 12 is in direct communication with the wearer's finger, and serves to shield the pulse sensor unit 12 from extraneous infrared energy sources.

Briefly, FIG. 3 illustrates the finger boot or shield 38 which may be utilized to shield the pulse sensor unit 12 from infrared interference. The shield 38 may be made of any suitable material which is opaque to IR energy, such as plastic or rubber, and has a circular opening 38a through which the sensor 12 is inserted. The necessity of additional shielding is determined by the particular sensors and electronics used. For example, the circuit of FIG. 1 provides for automatic cancellation of spurious signals and extra shielding may not be necessary.

Referring now to FIG. 4, the digital watch 10 has a pulse sensor unit 12 mounted into the receptacle 31 on its face. The pulse sensor 12 includes a transmitter diode 13 and a receiver diode 14 directed outwardly in a perpendicular direction to the plane of the watch face. Depressing the pulse sensor switch 27 activates the infrared detection electronics, causing the transmitter 13 to emit an IR signal. The wearer places his finger over the sensor 12 and the receiver diode 14 receives the reflected IR from the capillaries and tissues in the wearer's finger. The return signal is processed by the electronics within the watch and the pulse rate is periodically displayed on the display 30.

Referring now to FIG. 5, the watch 10 is illustrated with the pulse sensor unit 12 removed, thereby exposing the connector receptacle 31. The receptacle 31 may be a bayonette or screw type mounting and it should have a key 37a for aligning the pulse sensor unit 12 or the connector 33 with the receptacle 31. The key may be a pin that is machined into the receptacle 31. The individual contacts 31a-31d are illustrated as helical by shaped wire springs which make contact with the sensor 12 or the connector 33. Other types of contacts may be used instead, such as leaf spring-type contacts.

FIG. 6 illustrates the remote sensing cable arrangement 32 with the pulse sensor unit 12 attached to the sensor receptacle 36 (See FIG. 7) which is identical to the receptacle 31 on the watch. The cable connector 33 exposes the keyway 37b which is a slot cut into the printed circuit board 39 upon which the contacts 39a-39d are deposited. The cuff 34 is made of Velcro material, trade name of Velcro U.S.A. Inc., for easy snap-on and snap-off one-hand operation.

Figure 7:
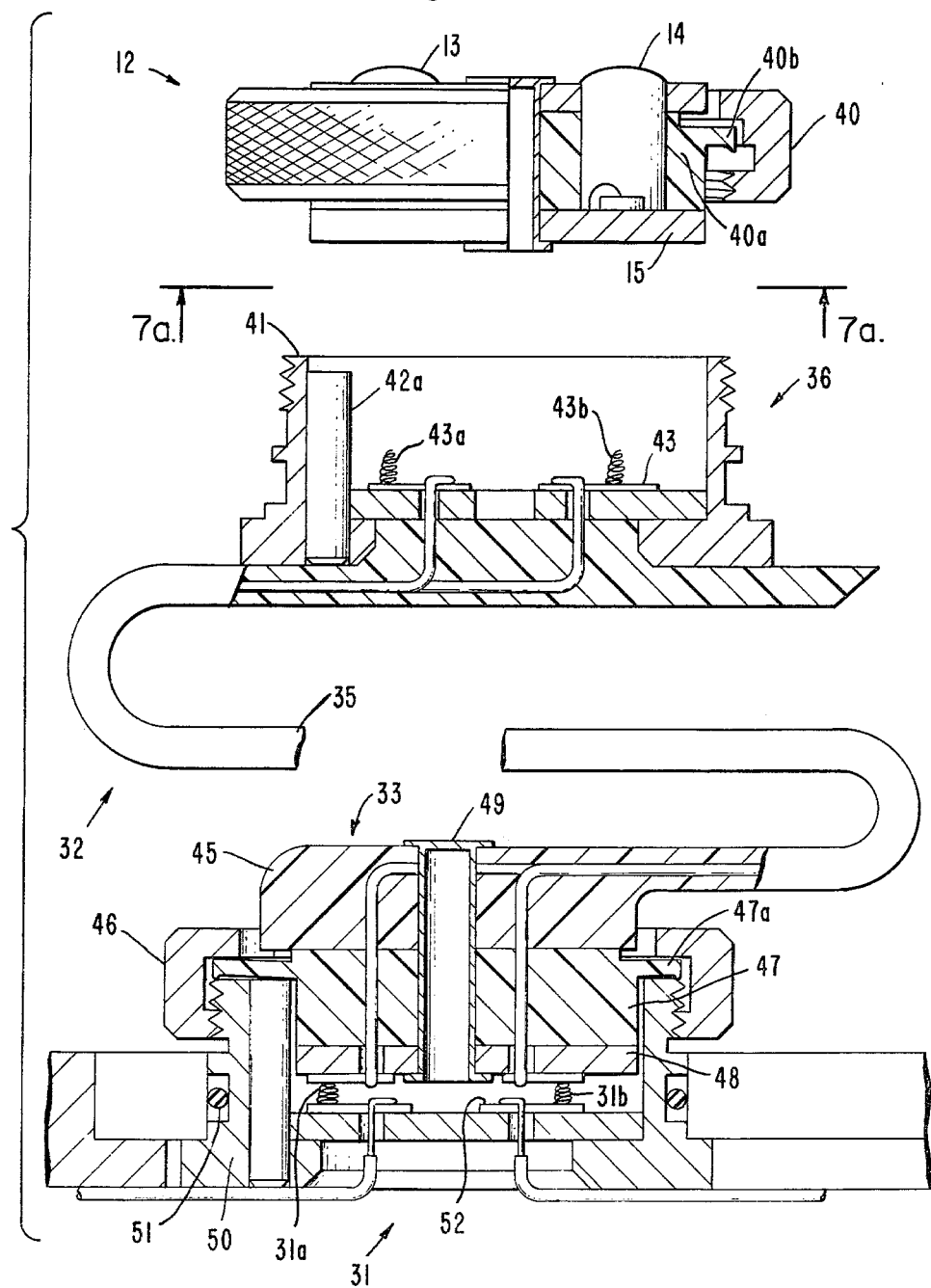
FIG. 7 is a cross-sectional view illustrating the detached transferable pulse sensor, the cable receptacle, and the connector mounted onto the watch receptacle.

FIG. 7 is a combination cross-sectional and exploded view of a sensor unit 12 in the sensor receptacle 36, and the cable connector 33 secured to the watch receptacle 31. The transmitter 13 and receiver 14 are assembled as a unit and the unit is free to rotate within the barrel or open centered cap 40 which screws onto the receptacle 36. The insulating body 40a has a circumferential lip 40b extending outwardly from its upper edge, which provides sealing for the sensor unit 12 to its respective receptacle. Both of the photodiodes 13 and 14 are mounted to a printed circuit substrate 15 having printed contact strips on its underside for making electrical contact with the receptacles.

Briefly, FIG. 7a illustrates the connection side of the pulse sensor unit 12 and depicts the printed circuit substrate 15 with its contacts 15a-15d and its keyway 42b. Both the connector 23 and the pulse sensor unit 12 are virtually identical when viewed from their connection sides.

Referring again to FIG. 7, the receptacle housing 41, attached to one end of the cable, includes an alignment key 42a for aligning the contacts of the sensor unit 12 to the contacts of the receptacle 36. Toward the bottom of the receptacle 36, a printed circuit type board 43 is located upon which four contacts, of which two, 43a and 43b are shown as conically shaped, are deposited or mounted. The wires from the cable 35 extend through the printed circuit board 43 and are soldered to their respective contacts.

At the bottom of the figure the cable connector 33 is shown connected to the watch receptacle 31. The top of the connector 33 is a plastic or insulating cap 45 through which the conductor wires are passed. The bottom of the cap 45 extends into the top of the connector barrel 46. Just below the cap 45 is an insulating body 47 and a printed circuit board 48 which has contacts printed thereon. The insulating body 47 has a circumferential lip 47a extending outwardly from its upper edge which provides sealing for the connector 33 when it is in place. The wires from the cable 35 extend through the insulating body 47 and the printed circuit board 48 where they are attached to their respective conductors. The cap 45, the insulating body 47 and the printed circuit board 48 are held together by a rivet 49. The receptacle housing 50, mounted on the watch face from the reverse side, has an O-ring 51 sealing the receptacle housing 50 to the watch face. A printed circuit board 52, upon which the contact springs 31a-31d are mounted, is situated toward the bottom of the housing 50.

In summary, what has been provided by the present invention is an interchangeable pulse sensor unit which is easily detachable from a receptacle on the face of a pulse sensing digital watch. The pulse sensor unit is mountable on one end of a remote pulse sensing cable which is attachable to a wearer's finger tip by a quick release cuff. The other end of the pulse sensing cable attaches to the watch receptacle. Thus, one may easily measure his pulse rate during strenuous exercises while his hands are free to do other things.

Although the present invention has been shown and described with reference to particular embodiments, nevertheless, various changes and modifications obvious to one skilled in the art to which the invention pertains are deemed to be within the purview of the invention.

I claim:

1. An infrared plethysmograph having a remote pulse sensing feature, comprising:
    pulse sensing electronics having a digital display and a receptacle for alternatively receiving either a pulse sensor unit or a remote sensing cable;
    a pulse sensor unit detachably mountable to said receptacle;
    a remote pulse sensing cable having a connector at a first end for mounting onto said receptacle, said cable having a receptacle at the second end for receiving said pulse sensing unit; and
    a cuff attached to said second end for securing said pulse sensing unit to a skin surface for sensing a pulse.

2. The invention according to claim 1 wherein said pulse sensor unit comprises:
    a transmitting unit; and
    a receiving unit.

3. The invention according to claim 2 wherein said transmitting unit comprises:
    a light emitting semiconductor device.

4. The invention according to claim 3 wherein said light emitting semiconductor device comprises:
    an infrared light emitting photodiode.

5. The invention according to claim 2 wherein said receiving unit comprises:
    a light receiving semiconductor device.

6. The invention according to claim 5 wherein said light receiving semiconductor device comprises:
    a photodiode.

7. The invention according to claim 6 wherein said semiconductors comprise:
    phototransistors.

8. The invention according to claim 1 wherein said removable pulse sensor unit comprises:
    an open-centered cap;
    a mounting substrate rotatably mounted within said open centered cap;
    a light emitting photodiode mounted on said mounting substrate and being visible through said open-centered cap; and
    a photodiode for receiving the reflected light from said light emitting photodiode mounted on said mounting substrate and being visible through said open-centered cap.

9. The invention according to claim 8 further comprising:
    contact means connected to said light emitting photodiode and said photodiode, said contact means disposed on said mounting substrate for making electrical contact with said electronics receptacle and said cable receptacle.

10. The invention according to claim 9 further comprising:
alignment means disposed on said pulse sensor unit for aligning said sensor unit to said electronics receptacle and said cable receptacle.

11. The invention according to claim 1 wherein said receptacles, said pulse sensor unit, and connector further comprise:
alignment means for aligning said pulse sensor unit and said connector with said receptacles.

12. The invention according to claim 11 wherein said alignment means of said receptacles comprise:
a key.

13. The invention according to claim 11 wherein said alignment means of said pulse sensor unit and said connector comprise:
a keyway.

14. The invention according to claim 1 wherein each of said receptacles further comprises:
at least three spring contacts electrically coupled to said pulse sensing electronics for engaging said pulse sensor unit.

15. The invention according to claim 1 wherein said pulse sensor unit further comprises:
a locking nut;
a rotatable substrate disposed within said locking nut;
an infrared transmitter element mounted on said substrate;
an infrared receiver element mounted on said substrate; and
at least three contacts mounted on said substrate for making electrical connection with said receptacle, said three contacts being coupled to said pulse sensing electronics.

16. The invention according to claim 1, wherein said removable pulse sensor unit and said remote pulse sensing cable connector further comprise:
sealing means for preventing contaminants from entering said sensor unit and said cable connector when said members are connected in their respective positions.

17. The invention according to claim 1 further comprising:
a finger boot for shielding said pulse sensor unit on said remote pulse sensing cable from ambient infrared energy.

* * * * *